(12) United States Patent
Rudolf von Rohr et al.

(10) Patent No.: US 10,370,501 B2
(45) Date of Patent: Aug. 6, 2019

(54) TREATMENT OF LIGNOCELLULOSIC BIOMASS WITH AROMATIC CHEMICALS AS SCAVENGERS

(71) Applicant: ETH Zurich, Zurich (CH)

(72) Inventors: Philipp Rudolf von Rohr, Basel (CH); Thomas Pielhop, Zurich (CH); Gastón Larrazábal Labrador, Zurich (CH)

(73) Assignee: ETH Zurich, Zurich (CH)

( * ) Notice: Subject to any disclaimer, the term of this patent is extended or adjusted under 35 U.S.C. 154(b) by 0 days.

(21) Appl. No.: 15/317,293

(22) PCT Filed: Jun. 15, 2015

(86) PCT No.: PCT/EP2015/063343
§ 371 (c)(1),
(2) Date: Dec. 8, 2016

(87) PCT Pub. No.: WO2015/193243
PCT Pub. Date: Dec. 23, 2015

(65) Prior Publication Data
US 2017/0137579 A1 May 18, 2017

(30) Foreign Application Priority Data
Jun. 17, 2014 (EP) ..................................... 14172819

(51) Int. Cl.
| C08H 8/00 | (2010.01) |
| C12P 19/02 | (2006.01) |
| D21C 1/02 | (2006.01) |
| D21C 3/22 | (2006.01) |
| D21C 9/00 | (2006.01) |
| D21C 11/00 | (2006.01) |
| C12P 19/14 | (2006.01) |
| D21C 5/00 | (2006.01) |

(52) U.S. Cl.
CPC ................ *C08H 8/00* (2013.01); *C12P 19/02* (2013.01); *C12P 19/14* (2013.01); *D21C 1/02* (2013.01); *D21C 3/222* (2013.01); *D21C 9/005* (2013.01); *D21C 11/0007* (2013.01); *C12P 2201/00* (2013.01); *D21C 5/005* (2013.01); *Y02E 50/16* (2013.01)

(58) Field of Classification Search
None
See application file for complete search history.

(56) References Cited

U.S. PATENT DOCUMENTS

| 2011/0302722 A1* | 12/2011 | Ashton | ................ | C12N 9/0061 |
| | | | | 8/102 |
| 2013/0045509 A1 | 2/2013 | Romero | | |
| 2014/0312270 A1* | 10/2014 | Pielhop | ................ | D21C 3/222 |
| | | | | 252/182.29 |

FOREIGN PATENT DOCUMENTS

| EP | 2559768 A1 | 2/2013 |
| WO | 2013068092 A1 | 5/2013 |

OTHER PUBLICATIONS

Zhang et al. Huanan Ligong Daxue Xuebao, Ziran Kexueban, 2012, 40(3), 22-29 (Year: 2012).*
Alvira et al. "Pretreatment technologies for an efficient bioethanol production process based on enzymatic hydrolysis: A review"; Bioresource Technology; 2010; pp. 4851-4861; vol. 101:13, Elsevier.
Berlin et al. "Inhibition of cellulase, xylanase and β-glucosidase activities by softwood lignin preparations"; Journal of Biotechnology, 2006; pp. 198-209; vol. 125:2, Elsevier.
Dorrestijn et al. "The occurrence and reactivity of phenoxyl linkages in lignin and low rank coal"; Journal of Analytical and Applied Pyrolysis; 2000; pp. 153-192; vol. 54:1-2, Elsevier.
Esteghlalian et al. "An Overview of Factors Influencing the Enzymatic Hydrolysis of Lignocellulosic Feedstocks"; Glycosyl Hydrolases for Biomass Conversion; 2001; pp. 100-111; vol. 769; American Chemical Society, Washington, DC.
Kubo et al. "Lignin-Based Polymer Blends and Biocomposite Materials"; Natural Fibers, Biopolymers, and Biocomposites; 2005; 27 pages, Taylor & Francis.
Li et al. "Lignin depolymerization/repolymerization and its critical role for delignification of aspen wood by steam explosion"; Bioresource Technology; 2007; pp. 3061-3068; vol. 98, Elsevier.
Li et al. "Improved lignin properties and reactivity by modifications in the autohydrolysis process of aspen wood"; Industrial Crops and Products; 2008; pp. 175-181; vol. 27, Elsevier.
Li et al. "Lignin monomer composition affects *Arabidopsis* cell-wall degradability after liquid hot water pretreatment"; Biotechnology for Biofuels; 2010; pp. 1-7; vol. 3:27, BioMed Central.
Lora et al. "Simulated autohydrolysis of aspen milled wood lignin in the presence of aromatic additives. Changes in molecular weight distribution"; Journal of Applied Polymer Science; 1980; pp. 589-596; vol. 25, John Wiley & Sons, Inc.
Lundquist et al. "Acid degradation of lignin. Part VII. The cleavage of ether bonds"; Acta Chem. Scand; 1972; pp. 2005-2023; vol. 26, No. 5.
Mosier et al. "Features of promising technologies for pretreatment of lignocellulosic biomass"; Bioresource Technology; 2005; pp. 673-686; vol. 96, Elsevier.
Palonen et al. "Adsorption of Trichoderma reesei CBH I and EG II and their catalytic domains on steam pretreated softwood and isolated lignin"; Journal of Biotechnology; 2004; pp. 65-72; vol. 107, Elsevier.
Pan et al. "Strategies to enhance the enzymatic hydrolysis of pretreated softwood with high residual lignin content"; Applied Biochemistry and Biotechnology; 2005; pp. 1069-1079; vol. 121-124, Humana Press.

(Continued)

*Primary Examiner* — Yun Qian
(74) *Attorney, Agent, or Firm* — The Webb Law Firm

(57) ABSTRACT

A method for using at least one compound as a scavenger, in particular as a scavenger in the hydrolytic treatment of lignocellulosic biomass is provided. The compound includes at least one aromatic ring substituted with at least two moieties each having a free electron pair, wherein the at least two moieties are arranged in meta-position to each other, and at least two alkyl or alkenyl moieties.

29 Claims, 4 Drawing Sheets

(56) References Cited

OTHER PUBLICATIONS

Radt et al. "Elsevier Encyclopedia of Organic Chemistry"; 1950; pp. 1210-1249; vol. 12B, Series III, Elsevier Publishing Company, Inc.
Sarkanen et al. "Lignins: occun-ence, formation, structure and reactions"; 1971; pp. 345-372.
Selig et al. "Enzymatic saccharification of lignocellulosic biomass—Laboratory analytical procedure (LAP)"; National Renewable Energy Laboratory; 2008; 8 pages; No. NREL/TP-510-42629.
Sluiter et al. "Determination of extractives in biomass—Laboratory analytical procedure (LAP)"; National Renewable Energy Laboratory; 2005; 12 pages; No. NREL/TP-510-42619.
Sluiter et al. "Determination of sugars, byproducts, and degradation products in liquid fraction process samples—Laboratory analytical procedure (LAP)"; National Renewable Energy Laboratory; 2006; 14 pages; No. NREL/TP-510-42623.
Sluiter et al. "Determination of structural carbohydrates and lignin in biomass—Laboratory analytical procedure (LAP)"; National Renewable Energy Laboratory; 2008; 17 pages; No. NREL/TP-510-42618.
Studer et al. "Lignin content in natural Populus variants affects sugar release"; PNAS Early Edition; 2010; 6 pages.
Voitl et al. "Analysis of products from the oxidation of technical lignins by oxygen and H3PMo12O40 in water and aqueous methanol by size-exclusion chromatography"; Holzforschung; 2010; pp. 13-19; vol. 64, Walter de Gruyter.
Wade. Organic Chemistry; 2006; 6th ed.; Prentice Hall. (English-language abstract only).
Wayman et al. "Aspen autohydrolysis—The effects of 2-naphtol and other aromatic compounds"; Tappi; 1978; pp. 55-57; vol. 61:6.

\* cited by examiner

1: aromatic core
2: activating groups
3: blocking groups
4: active site

TREATMENT OF LIGNOCELLULOSIC BIOMASS WITH AROMATIC CHEMICALS AS SCAVENGERS

CROSS-REFERENCE TO RELATED APPLICATIONS

This application is the United States national phase of International Application No. PCT/EP2015/063343 filed Jun. 15, 2015, and claims priority to European Patent Application No. 14172819.6 filed Jun. 17, 2014, the disclosures of which are hereby incorporated in their entirety by reference.

BACKGROUND OF THE INVENTION

Field of the Invention

The present invention relates to a method for using an aromatic compound as a scavenger, a process for the production of a cellulosic feedstock by hydrolytic treatment of lignocellulosic biomass, cellulosic feedstock and lignin fraction.

Description of Related Art

Lignocellulosic biomass like wood, forest and agricultural residues or grass crops are a renewable source for the production of chemicals and fuels. A possible approach is the biochemical upgrading route by enzymatic hydrolysis of cellulose and hemicellulose to monomeric sugars, followed by fermentation to the final product. The lignin fraction of the biomass can be burned for the production of heat but is also a prospective source for the production of aromatic chemicals due to the aromatic structure of the lignin polymer.

The lignin and its entanglement with cellulose and hemicellulose however, protect the biomass from external influences like enzymatic attacks. Lignin can hinder the enzymatic hydrolysis by acting as a physical barrier, restricting the accessibility of cellulose to enzymes (Esteghlalian Ali & Srivastava et al., 2000), but also by non-productive binding of cellulolytic enzymes (Berlin & Balakshin et al., 2006; Esteghlalian Ali et al., 2000). The hindrance by lignin is one of the main reasons why a pretreatment of the biomass, which can break down the lingo-cellulose structure or even remove the lignin, is necessary prior to enzymatic hydrolysis.

Autohydrolysis treatment methods (in this document defined as methods that include hot-water and/or steam treatment) are attractive regarding their cost-savings potential (Alvira & Tomas-Pejó et al., 2010). They do not require acid, base or solvent chemicals and accordingly simplify a biorefinery process. The need for neutralisation chemicals is reduced (Mosier & Wyman et al., 2005) and the removal of a lignin solvent, which can be inhibitory to enzymes and fermentative microorganisms (Alvira et al., 2010), is not necessary.

In autohydrolysis pretreatments, lignin is hardly removed and remains in the solid phase together with cellulose, while hemicellulose is easily solubilised and removed (Alvira et al., 2010). This lack of lignin removal is one reason why autohydrolysis pretreatments are not very effective for several types of biomass that show an increased recalcitrance to enzymatic hydrolysis (e.g. softwood). Another important factor are repolymerisation reactions of the lignin which take place during the pretreatment, as will be disclosed later in this document. In autohydrolysis, organic acids like acetic acid are released from hemicellulose (Mosier et al., 2005) leading to moderate acidic conditions of typically pH 2-4, depending on the type of biomass, load and pretreatment severity. Many authors have established that under acidic treatments of wood, carbonium ions are formed in the lignin molecule that are responsible for the repolymerisation reactions (Sarkanen & Ludwig, 1971; Wayman & Lora, 1978). In today's chemical terminology, those three-coordinate carbon ions are denoted as carbenium ions, but will be named carbocations in this document to avoid misconceptions with existing literature. Those carbocations have been identified as intermediates in lignin depolymerisation reactions, especially in the cleavage of β-arylether linkages as shown in FIG. 1 (route a-c). On the other hand, the electrophilic carbocations are also able to form, through substitution, stable C—C bonds with the electron rich carbon atoms of the aromatic rings present in lignin (Sarkanen & Ludwig, 1971; Wayman & Lora, 1978) (FIG. 1 route a-d). High-molecular weight, condensed and insoluble lignin structures are formed (Wayman & Lora, 1978). Such condensed lignin structures form an additional obstacle for enzymatic hydrolysis, as will be specified later in this document.

A method for suppressing undesired lignin repolymerisation reactions is the use of carbocation scavengers. Wayman and Lora (Wayman & Lora, 1978) first reported that certain aromatic compounds can act as scavengers in an autohydrolysis extraction process. In such a process, aspen wood could be separated into its three main components using autohydrolysis followed by extraction with a suitable solvent. The addition of certain compounds in aspen autohydrolysis increased the yield of organic solvent-extractable lignin, allowing to obtain a highly delignified pulp for paper production. The additives were believed to act as scavengers, competing with the aromatic rings present in the lignin for the formed carbocations and prevent repolymerisation reactions. This yielded a lignin of lower molecular weight and enhanced its extractability (Wayman & Lora, 1978). In that way, it became possible to carry out the autohydrolysis at lower temperatures, while still obtaining a well extractable lignin. Due to the lower autohydrolysis temperature, less cellulose got depolymerised and therefore a better fiber quality of the pulp could be obtained with the autohydrolysis extraction process. 2-naphtol was found to be a very effective additive/scavenger and later studies treating isolated lignin in acidified hot water could confirm that the presence of 2-naphtol decreases the molecular weight of the resulting lignin (Li, Henriksson et al., 2007; Lora & Wayman, 1980). 2-naphtol was believed to be an effective lignin carbocation scavenger for two reasons. It is a strong nucleophile so it can attack the positively charged carbocations, plus it preferably undergoes just a single electrophilic substitution, thereby not promoting lignin crossing reactions (Wayman & Lora, 1978). 2-naphtol is easily substituted in position 1 (Radt, 1950), but not in position 3 as in this case the transition state can only be stabilised by the OH group in a non-aromatic structure (Wayman & Lora, 1978). As the complete loss of aromaticity (i.e. over the whole molecule) in the transition state is energetically very costly, 2-naphtol preferably undergoes a single substitution in position 1. The essential mode of action of this scavenger is therefore controlled by the loss/preservation of aromaticity when substituted on different positions.

It has recently been shown that the use of carbocation scavengers in the autohydrolysis of lignocellulosic biomass can also improve its enzymatic digestibility (Studer, Pielhop et al., 2013). The cellulose conversion in the enzymatic hydrolysis of spruce was improved up to 46% by adding 2% w/w (relative to biomass load) of 2-naphtol to a hot-water pretreatment. Surprisingly, the enhancement in digestibility was not based on an increased lignin removal during the pretreatment. The effect was therefore attributed to a potentially different lignin structure in the pretreated biomass, which increases the cellulose accessibility.

However, there is still a desire to further improve the autohydrolysis of lignocellulosic biomass and suppressing the undesired lignin repolymerisation.

SUMMARY OF THE INVENTION

It is therefore an object of the present invention to provide an approach for improving or enhancing the breakdown of lignocellulosic biomass in an autohydrolysis treatment and enhancing the enzymatic digestibility of cellulose obtained from said autohydrolysis treatment.

This object is being solved by a method for using at least one compound with the features as described herein and a process as described herein.

Accordingly, at least one compound is used as a scavenger, in particular as a scavenger in the hydrolytic treatment of lignocellulosic biomass, wherein the compound comprises at least one aromatic ring substituted with at least two moieties each having a free electron pair, wherein the at least two moieties are arranged in meta-position to each other, and at least two alkyl or alkenyl moieties.

The moieties on the aromatic ring having at least one free electron pair (or lone pair), such as —OH, —NH$_2$, —NR$^x{}_2$ or halogen groups, which increase the electron density in the aromatic ring. The increased electron density in turn provides a high reactivity with a carbocation and thus guarantees a high scavenging effect. Moreover, those moieties, as all activating substituents, direct substitutions towards ortho- and para-positions.

In an embodiment of the present invention the at least one compound used as a scavenger, in particular as a carbocation scavenger is selected from at least one compound of
the general formula (I)

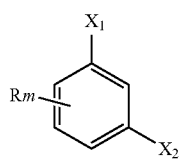

wherein
X$_1$, X$_2$=OH, NH$_2$ or NR$^x{}_2$,
R, R$^x$=unsubstituted or substituted alkyl or unsubstituted or substituted alkenyl,
m=2 or 3, which preferably occupy two of the three ortho positions of X$_1$ and X$_2$, or
the general formula (II)

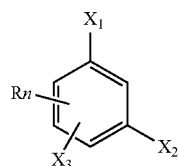

wherein
X$_1$, X$_2$, X$_3$=OH, NH$_2$ or NR$^x$, wherein X$_3$ is in particular in meta-position to X$_1$ and X$_2$;
R, R$^x$=unsubstituted or substituted alkyl or unsubstituted or substituted alkenyl,
n=2, or
the general formula (III)

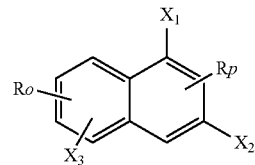

wherein
X$_1$, X$_2$=OH, NH$_2$ or NR$^x$,
X$_3$=absent or OH, NH$_2$ or NR$^x$,
R, R$^x$=unsubstituted or substituted alkyl or unsubstituted or substituted alkenyl
o=0 to 4,
p=1,
or a mixture thereof.

In a preferred embodiment the compound presently used as a scavenger, in particular as carbocation scavenger, is selected from a group consisting of

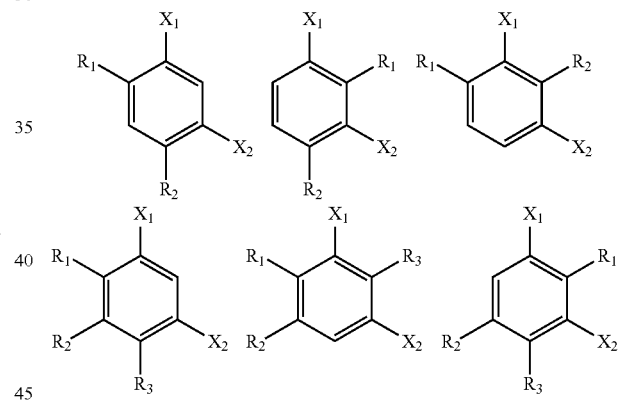

wherein X$_1$, X$_2$ have the above meanings, and R$_1$, R$_2$ and R$_3$ have the meaning of R and can be the same or different.

It is also preferred to use a compound as scavenger, in particular as carbocation scavenger, wherein the compound is selected from a group consisting of

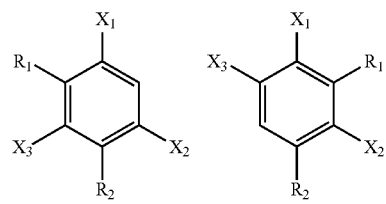

wherein X$_1$, X$_2$, X$_3$ have the above meanings, and R$_1$ and R$_2$ have the meaning of R and can be the same or different.

In an even more preferred embodiment the compound presently used as a carbocation scavenger is one of the following compounds

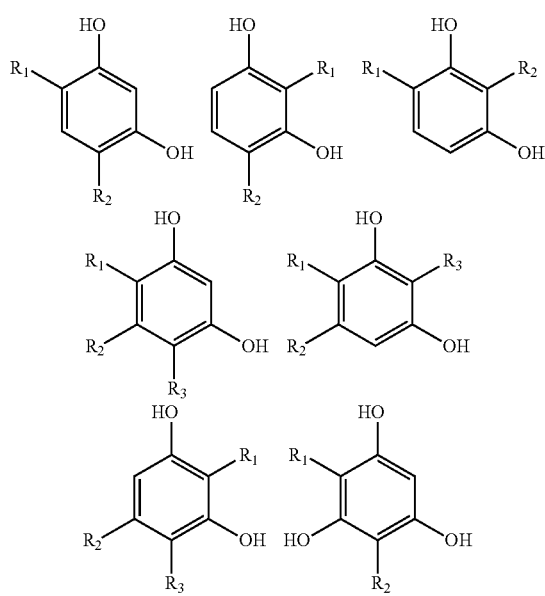

wherein $R_1$, $R_2$ and $R_3$ have the meaning of R and can be the same or different.

In a further embodiment the moieties R, $R_1$, $R_2$, $R_3$, and $R^x$ of the presently used compound are a $C_1$-$C_{10}$ alkyl or $C_1$-$C_{10}$ alkenyl moiety, in particular a $C_1$-$C_5$ alkyl or $C_1$-$C_5$ alkenyl moiety. It is preferred, if R, $R_1$, $R_2$ and $R_3$ is a methyl, ethyl, n-propyl, i-propyl, n-butyl, i-butyl, t-butyl, propenyl, butenyl and/or pentenyl moiety.

The term "substituted" used in conjunction with "alkyl" or "alkenyl" defines the substitution of one or multiple atoms, usually H-atoms, by one or multiple of the following substituents: halogen, hydroxy, protected hydroxy, oxo, protected oxo, $C_3$-$C_7$-cycloalkyl, bicyclic alkyl, phenyl, naphtyl, amino, protected amino, monosubstituted amino, disubstituted amino, guanidino, protected guanidino, heterocyclic ring, substituted heterocyclic ring, imidazolyl, indolyl, pyrrolidinyl, $C_1$-$C_{12}$-alkoxy, $C_1$-$C_{12}$-acyl, $C_1$-$C_{12}$-acyloxy, acryloyloxy, nitro, carboxy, protected carboxy, carbamoyl, cyano, methylsulfonylamino, thiol, $C_1$-$C_{10}$-alkylthio and $C_1$-$C_{10}$-alkylsulfonyl. The substituted alkyl or alkenyl moieties can be substituted once or multiple times, preferably once or twice, with the same or a different substituent.

The term "cycloalkyl" comprises the groups of cyclopropyl, cyclobutyl, cyclopentyl, cyclohexyl and cycloheptyl.

In an embodiment the moieties R, $R_1$, $R_2$, $R_3$, and $R^x$ of the presently used compound are a $C_1$-$C_{10}$ alkyl or $C_1$-$C_{10}$ alkenyl moieties substituted with a functional group such as —OH, —$NH_2$, —$CO_2H$, —$COR^y$ (with $R^y$ being an alkyl or alkenyl moiety, in particular a $C_1$-$C_{10}$ alkyl or $C_1$-$C_{10}$ alkenyl moiety) or halogen (such as Cl, Br, I).

In a most preferred embodiment compound presently used as carbocation scavengner is selected from a group comprising dimethylphloroglucinol, 3-hydroxy-4,5,6-trimethylphenol, 3-hydroxy-2,5,6-trimethylphenol, 3-hydroxy-2,4,5-trimethylphenol, 3-hydroxy-4,6-dimethylphenol, 3-hydroxy-2,6-dimethylphenol, 3-hydroxy-2,4-dimethylphenol, wherein dimethylphloroglucinol is in particular useful.

The concept of the present invention differs substantially from previous approaches. The invention describes an autohydrolysis process of lignocellulosic biomass with the use of specially devised carbocation scavengers, followed by enzymatic hydrolysis of the cellulose and/or hemicellulose for the production of fermentable sugars (see FIG. 2). The process does not separate wood into its three main components, extract lignin or produce pulp, but degrades the biomass biologically. Cellulose is not preserved but digested to its sugars. The autohydrolysis in this process does not aim for low temperatures to preserve cellulose, but in contrast for high temperatures which improve the opening up of the biomass structure.

Specially devised scavengers prevent lignin condensation in the autohydrolysis, and in that way enhance the enzymatic digestibility of the biomass. The reason for the increased digestibility is that the less condensed lignin features a considerably smaller specific surface area (experimental results not shown) and less enzymes get adsorbed/deactivated on the lignin. Due to the modified lignin, more enzymes remain available for the actual hydrolysis of the cellulose and/or hemicellulose and sugar yields are increased. The cellulose accessibility is not influenced by the scavenger (experimental results not shown).

The scavengers presented in this invention are a new class of specially activated (lignin) carbocation scavengers that have not been described before. They consist of four constituents (see also FIG. 3):
1. One or several aromatic rings, that form the basis of the scavenger molecule.
2. Functional groups that additionally activate the molecule towards electrophilic substitution.
3. Blocking groups that block excessive activated positions of the aromatic ring for electrophilic substitution.
4. Preferably a single active site, that reacts with the lignin.

This simple but effective structure allows to devise scavengers which are strongly activated for electrophilic substitution but undergo preferably only a single electrophilic substitution, thereby not promoting lignin crossing reactions. The scavenging effect is not based on the preservation/loss of the molecule aromaticity like e.g. in 2-naphtol (compare FIG. 4), but on the targeted activation and blocking of reactive sites of the molecule.

The main objects of the present invention can be summarized to the following points:
Prevent lignin condensation in autohydrolysis or acid treatments of lignocellulosic biomass by specially devised lignin carbocation scavengers. The scavengers effect is based on the targeted activation and sterical blocking of reactive sites of the aromatic molecule.
Decrease enzyme adsorption in the enzymatic hydrolysis of the lignocellulosic biomass due to the prevention of lignin condensation in the preceding autohydrolysis or acid treatment.
Provide a low cost and environmentally superior pretreatment process.

The invention covers the three basic areas of a typical biorefinery: pretreatment, hydrolysis & fermentation and lignin valorisation, which are closely related to each other (FIG. 2).

Therefore a process for the treatment and the production of a cellulosic feedstock by hydrolytic treatment of lignocellulosic biomass is provided wherein at least one compound described in detail above is added to the lignocellulosic biomass before, during and/or after the aqueous treatment (autohydrolysis) of the lignocellulosic biomass. This process allows for providing cellulosic feedstock which may subsequently enzymatically converted to sugars and even further to alcohols or other small organic compounds.

The autohydrolysis treatment is the first step in this invention. A scavenger (as described above) is used, which is effective in suppressing lignin condensation regarding the subsequent saccharification. Preferably, it also results in a favourable lignin depolymerisation regarding final lignin products.

The previously described scavenger compounds can be used in the process as solid, liquid or gaseous compounds. Those include especially monocyclic but can also include polycyclic aromatics.

The underlying mechanism of improving the biomass digestibility by the scavenger is that lignin condensation in autohydrolysis is prevented. Lignin condensation decreases the pore size and increases the number of pores in the lignin, so that its specific surface area is increased (experimental results not shown). When using a scavenger, the specific lignin surface area is significantly decreased, so that less enzymes are able to adsorb on the lignin and remain active in the enzymatic hydrolysis of the cellulose.

Any lignocellulosic material containing fermentable carbohydrate (e.g. softwood, hardwood, herbaceous biomass, agricultural residues) with an open structure can serve as raw material for the autohydrolysis treatment. Sawdust, wood flour and chips as well as wood splinters and slivers can also be used in accordance with the present invention, without any preceding chipping or destructuration. Preferred raw materials are softwoods such as spruce, pine or larch. Softwood is considered particularly recalcitrant for hydrolysis owing to the higher amount and nature of its lignin (Pan & Xie et al., 2005). An effective pretreatment overcoming this resistance is therefore especially favorable for this kind of lignocellulose, as pointed out in the following:

The autohydrolysis process as presented in this invention is favorably in this perception, as softwood lignin contains mainly guaiacyl (G) units, while hardwood lignin contains mixed guaiacyl and syringyl (S) units. It is well known that native lignins with low S/G ratios present a much higher degree of condensed C—C bonds at the C-5 site of the aromatic ring (5-5 and β-5 linkages (Dorrestijn & Laarhoven et al., 2000), since the C-5 position in guaiacyl units is not blocked by a methoxyl group like in syringyl units (compare FIG. 1). It suggests itself that guaiacyl units could also be more prone to condensation reactions during autohydrolysis, offering an extra ring position for substitution. Noteworthy in this respect, the C-5 position could even be additionally activated towards electrophilic substitution by the adjacent hydroxyl group, donating electron density (inductive effect) and stabilising the carbocation in the transition state by resonance (mesomeric effect). Different studies (Li & Ximenes et al., 2010; Studer & DeMartini et al., 2011) have reported that a decrease in the S/G ratio of lignin in biomass samples gave rise to a significant decrease in glucose release from enzymatic hydrolysis after an autohydrolysis pretreatment. Surprisingly, the S/G ratio had no influence on sugar release when no pretreatment was carried out. Next to the more difficult cleavage of the more condensed bonds in samples with low S/G ratios (Studer et al., 2011), an increase in condensation reactions with increasing guaiacyl content might also play a role in this effect. The S/G ratio of softwoods is exceptionally low (Dorrestijn et al., 2000), suggesting that condensation reactions play an important role in autohydrolysis and the presented invention has an increased effect on softwood types of wood. Nevertheless, the proposed process can also prove beneficial for hardwood and any other lignocellulosic resources.

The lignocellulosic material can be treated as a suspension in a liquid phase and/or directly with steam. Thus, the aqueous treatment of the lignocellulosic biomass may be a liquid hot water treatment or an aqueous steam treatment. Steam treatment methods are preferred, as they allow for high solids concentration as favoured in commercial operations. Steam pretreatments also allow for a steam "explosion" by the rapid release of pressure after the autohydrolysis treatment. This helps defibrating the biomass which can be beneficial for the enzymatic hydrolysis and/or the further processing of the biomass slurry (easier pumping). Depending on the reactor system used, the water to dry biomass ratio can be in the range between 1:5 and 100:1, preferably between 1:1 and 5:1. Preferred reactor types for the hot water treatment are (stirred) tank or steam (explosion) reactors that can be operated in batch or continuous mode. Other possible types of reactors include for example tubular reactors or reactors where the lignocellulosic material is packed in a slowly moving bed and the fluid or steam may be in either concurrent or countercurrent flow.

The scavenger can be added for example by simple mixing with the biomass or impregnation of the biomass prior to autohydrolysis treatment or by direct addition to the liquid water or steam phase. The quantity of the scavenger added in autohydrolysis may vary in a wide range between 0.01 to 20% w/w based on dry biomass loading. An optimum scavenger loading in autohydrolysis aims at a good treatment of the biomass for enzymatic hydrolysis and a complete conversion of the scavenger. A complete conversion means that a possible inhibition of the enzymatic hydrolysis or fermentation by the scavenger can be excluded.

The autohydrolysis treatment can be carried out for example under an atmosphere consisting or containing an inert gas, oxygen, ozone, $CO_2$ or hydrogen, preferably under inert gas or air. The temperature in the autohydrolysis treatment step is maintained within the range from about 100 to 260° C., preferably from about 200 to 240° C. The duration of the treatment can vary from less than one minute to several days as long as the particle structure is thoroughly penetrated. At higher temperatures, a shorter treatment time is required. For example a retention time of 3 to 60 minutes can suffice at 190 to 240° C., while 60 minutes to several hours may be necessary to obtain the desired result at temperatures lower than about 190° C. It is also possible to carry out a multi-step treatment. For example a mild treatment stage at lower temperatures (or short treatment times) followed by a harsher treatment stage at higher temperatures (or longer treatment times). In that way, dissolved hemicellulosic sugars can be recovered after the first treatment stage. The separated biomass can then undergo a harsher treatment for improving the cellulose digestibility. The second treatment stages includes the use of scavengers for preventing lignin condensation reactions, which especially occur at harsh treatments.

The pH during autohydrolysis treatment preferably lies in the range between about 2 and 4 due to the release of organic acids from the biomass. However, the pH can be lowered further by the addition of acids to enhance the breakup of the lignocellulose structure. The scavenger is likely to be even more effective as carbocations in lignin are especially formed under acid conditions. Inorganic acids such as nitric acid, hydrochloric acid or phosphoric acids and organic acids such as acetic or formic acid may be added.

In another embodiment of the present process the pH during the aqueous treatment of the lignocellulosic biomass is adjusted by the addition of bases, as for example inorganic bases like alkali salts such as sodium hydroxide and organic bases such as pyridine. This may be necessary if the pH drops during the pretreatment step of the biomass to values between 3 and 4 due to the release of free acids.

In the autohydrolysis treatment step, biomass with a highly digestible cellulose and preferably a high quality, pre-depolymerised lignin are to be produced. The biomass is to be pretreated as well as possible, however without decomposing the desired sugar products or producing a lot of toxic compounds for enzymatic hydrolysis and fermentation. Therefore, this approach represents an optimisation task regarding suitable carbocation scavengers, temperature, time etc.

As mentioned previously, the cellulosic feedstock obtained by hydrolytic treatment of lignocellulosic biomass can be used for further enzymatic degradation by suitable enzymes such as cellulases, amylases and/or ligninases. The objective for hydrolysis is a high digestibility of the cellulose, i.e. a high sugar yield and a short residence time, while using small amounts of enzyme.

In the course of the hydrolytic treatment an enzyme complex is added which degrades cellulose to sugars. This enzyme complex may comprise as cellulases for instance endo-1,4-beta-D-glucanase, beta-1,4-endoglucan hydrolase, and others. Some of the cellulase degrading enzymes degrade cellulose at the ends thereof and produce cellobiose, while others degrade cellobiose to glucose molecules (such as two glucose molecules). The enzymatic hydrolytic treatment is preferably carried out at a pH between 4.5 and 6, preferably at 5 and at temperatures between 40 and 60° C., preferably at 50° C.

For the present process, the enzymatic hydrolysis of spruce sawdust, that was autohydrolysis treated without additive, can serve as a benchmark. An Experiment using dimethylphloroglucinol as a representative scavenger structure, proves the use of the described carbocation scavengers in autohydrolysis treatments feasible for enhancing enzymatic hydrolysis (compare FIG. 8). The glucose yield was increased by 42% after the autohydrolysis treatment with 4.24% w/w (based on raw dry biomass) of Dimethylphloroglucinol compared to the control. These results show that due to the suppression of lignin condensation the enzymatic digestibility of the cellulose is improved.

The inhibition of enzymatic hydrolysis and fermentation through byproducts from autohydrolysis treatment (e.g. furfurals) and remaining unreacted scavenger is possible. This can be prevented by washing the biomass prior to hydrolysis. From a process engineering point of view, a process without washing is economically favourable. Therefore, either a complete consumption of the scavenger or the use of a non-toxic scavenger is preferred. A reduction of severity in the autohydrolysis treatment, as allowed for by an effective scavenger, can also prevent the formation of inhibiting compounds from the biomass.

The remaining biomass after a complete enzymatic hydrolysis basically consists of lignin. This lignin has already been partially depolymerised as a result of the autohydrolysis treatment. As stated earlier, this depolymerisation will even have proceeded further than usual due to the suppression of lignin repolymerisation reactions by the scavenger which can yield a much more uniform and homogeneous lignin structure. Such a lignin fraction, with a low and more defined molecular mass and in particular less condensed C—C bonds, can be assumed to have a much higher chemical value and prove beneficial for the production of chemicals, especially for the production of aromatic monomers. Noteworthy, the scavengers can be integrated into the structures of the later produced chemicals.

Generally, a challenge in the production of chemicals from lignin is that complex product mixtures are obtained. However, when using the lignin products as a scavenger mixture for an autohydrolysis treatment, this is less problematic.

It is also possible, to recover the scavengers used in the autohydrolysis treatment by a laccase treatment of the obtained lignin. Laccases could specifically break scavenger-lignin bonds to release the scavenger again and recycle it to the autohydrolysis treatment stage.

The produced lignin is also attractive from a polymer chemistry point of view, for the use as a component in phenol-based polymers. Available commercial lignins have limited utility in applications which demand a constant well-defined feedstock, due to inherent chemical and molecular weight inhomogeneity (Satoshi, Richard et al., 2005). In the proposed process, lignins with a low, more defined molecular mass, preferably in a range between 500 and 5000 g/mol, and good solubility can be produced.

Together with the efficient incorporation of aromatic scavengers into the lignin leading to a high number of corresponding phenolic sites, this should make such lignins attractive as a component for phenol-based polymers (Li & Gellerstedt, 2008). Noteworthy, the scavengers can be integrated into the lignin structure for improving interaction with the polymer.

Several substances were evaluated as additives in the autohydrolysis and enzymatic hydrolysis process.

Compounds were selected based on two main goals:

(1) to evaluate compounds that allow the establishment of relationships between the glucose yield in hydrolysis and the structure and reactivity of the scavenger (explicitly including compounds that decrease sugar yields) and based on these findings (2) to identify substances that are able to act as carbocation scavengers and improve glucose yields in enzymatic hydrolyis.

It is important to recall that a nucleophile (or Lewis base) is a substance that can donate an electron pair to form a new chemical bond. The counterpart that accepts the electron pair is called an electrophile (or Lewis acid) (Wade, 2006). In this context, the carbocation on the lignin structure and the scavenger correspond to the electrophile and the nucleophile, respectively Due to the lone pairs of electrons on the oxygen atom, alcohols may act as nucleophiles. Although aliphatic alcohols are typically weak nucleophiles, they can react with carbocations (which are very strong electrophiles) to form new C—O bonds (Wade, 2006), as shown in FIG. 5. Primary alcohols are better nucleophiles than secondary alcohols, which are better than tertiary alcohols. Three aliphatic alcohols were evaluated: methanol ($CH_3OH$), ethanol ($CH_3CH_2OH$) and 2-propanol (($CH_3)_2CHOH$, a secondary alcohol).

Aromatic alcohols, of which phenol is the simplest example, behave very differently to their aliphatic counterparts. Substitution does not occur on the oxygen atom but rather on the aromatic ring because the OH group strongly activates the ring towards electrophilic aromatic substitution. Moreover, the OH group, as all activating substituents, directs substitution towards ortho and para positions (Wade, 2006). The structures of the evaluated aromatic alcohols, including 2-naphthol, are shown in FIG. 6.

Compounds with more than one OH group are expected to be more reactive than phenol because the hydroxyl group donates electron density to the aromatic ring (inductive effect) and helps stabilize the formed carbocation by resonance (mesomeric effect). The three benzenediol isomers are expected to have different tendencies towards lignin crossing reactions/bridging and were therefore included in the screening. Phloroglucinol is activated by three OH groups and is considered to be an especially active bridging agent. Occupying two of the three free ring positions on phloroglucinol with a methyl group gives dimethylphloroglucinol, which should not be able to act as a crossing agent but as an effective blocking agent/scavenger.

BRIEF DESCRIPTION OF THE DRAWINGS

The present invention will now be explained in more detail by means of the examples with reference to the Figures.

DETAILED DESCRIPTION

I. Reagents

Figure 5:
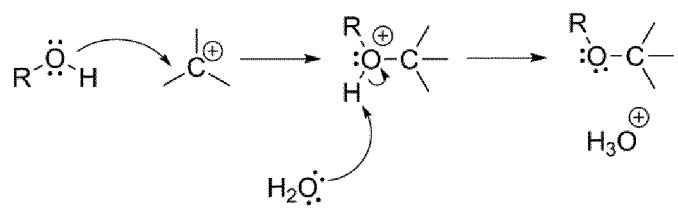
FIG. 5 a scheme showing the reaction of an aliphatic alcohol and carbocation.
Figure 6:
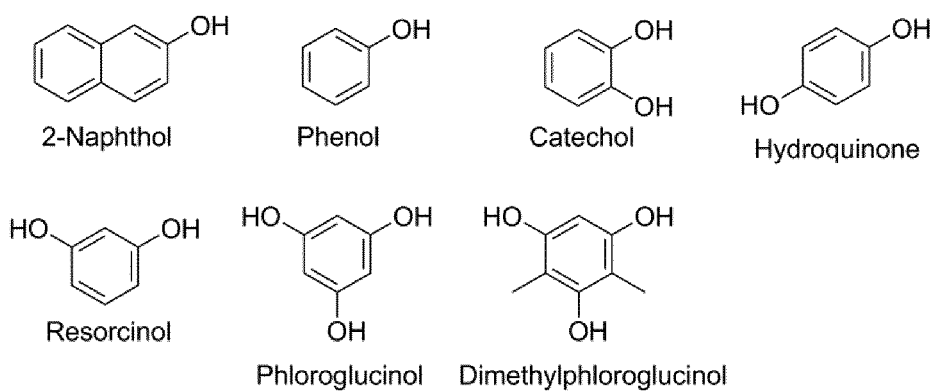
FIG. 6 structures of different compounds tested for their scavenging activity.

The following compounds were evaluated as additives (see also FIGS. 5 and 9): 2-naphtol (Fluka, ≥99%), methanol (Fluka, ≥99.8%), ethanol (Fluka, ≥99.8%), 2-propanol (Scharlau, ≥99.8%), phenol (Fluka, ≥99%), resorcinol (Chemie Brunschwig, 98%), catechol (Sigma-Aldrich, ≥99%), hydroquinone (Sigma-Aldrich, ≥99%), phloroglucinol dihydrate (Aldrich, 97%), dimethylphloroglucinol (Green Pharma, ≥95%).

Figure 1:
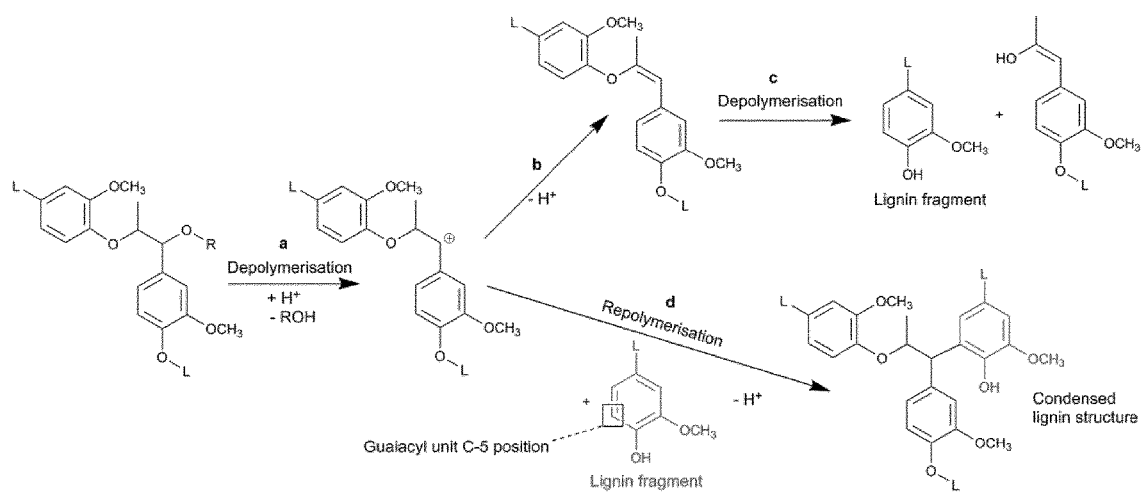
FIG. 1 a scheme for lignin reaction in acidic media.
Figure 2:
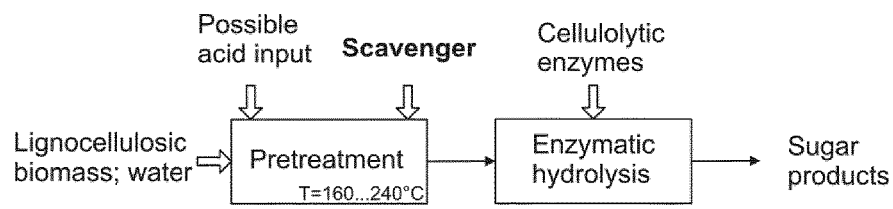
FIG. 2 a process scheme for biological conversion of lignocellulose biomass to sugars.
Figure 3:
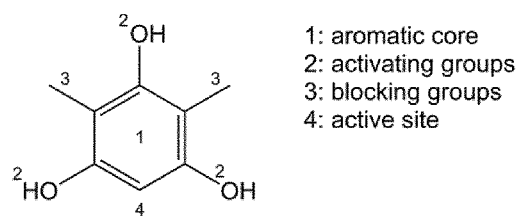
FIG. 3 an embodiment of a preferred scavenging compound.
Figure 4:
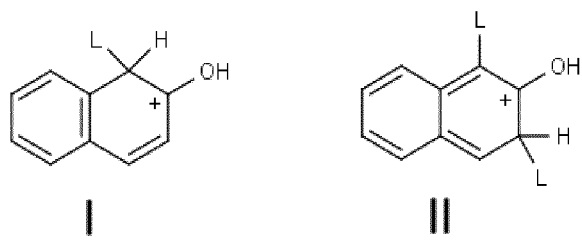
FIG. 4 a scheme showing different transitions states of 2-naphthol as scavenger.

II. Autohydrolysis Treatment, Biomass Analysis and Enzymatic Hydrolysis (FIG. 2)

Spruce wood, sourced from a forest in the canton of Solothurn, Switzerland and previously knife-milled through a 1 mm screen size in a Retsch SM200 cutting mill, was sieved with a Retsch AS200 vibratory sieve shaker to obtain a particle size fraction between 0.18 and 1 mm. The spruce dry matter (74.63±0.39% w/w) composition was determined by standard NREL methods (Sluiter & Hames et al., 2008; Sluiter & Ruiz et al., 2005): glucan 45.18±0.55%, mannan 17.74±0.28%, acid soluble lignin (ASL) 4.77±0.42%; acid insoluble lignin (AIL) 28.73±0.06%, extractives 4.89% and ash 0.22%±0.01 (total 101.53%).

The autohydrolysis treatment of the biomass was carried out in a Parr MRS 5000 Multi-Reaction system, which consists of six 75 mL stainless steel reactors, each equipped with a suspended magnetic stirrer. Heat is provided to each reactor through an electrically heated aluminum external jacket. The reactor was loaded with 2.5 g of spruce wood (including moisture) and 39.2 g of distilled water, resulting in a biomass loading of 6% w/w. The amount of the autohydrolysis additive depended on its molar mass. For comparison reasons, All additives were dosed at the same molar ratio of 0.2054 mol scavenger/mol lignin C9 unit. This molar ratio is the same as in the pretreatment of biomass with 2-naphthol at a loading of 4% w/w of the biomass load, which was used as a benchmark. The corresponding concentrations of each additive are shown in Table 1.

TABLE 1

Autohydrolysis additive loadings for biomass autohydrolysis as weight percentage of the amount of biomass (including moisture) in the reactor.

| Substance | Loading/% w/w |
| --- | --- |
| Methanol | 0.89 |
| Ethanol | 1.28 |
| 2-Propanol | 1.67 |
| 2-Naphthol | 4.00 |
| Phenol | 2.61 |
| Resorcinol | 3.05 |
| Cathechol | 3.05 |
| Hydroquinone | 3.05 |
| Phloroglucinol | 3.50 |
| Dimethylphloroglucinol | 4.24 |

Before the autohydrolysis treatment the reactor was purged three times with nitrogen at 15 bar and the stirrer speed was set at 400 min$^{-1}$. The reaction temperature of 210° C. was reached in approximately 12 minutes by preheating the aluminum jacket to 350° C. before inserting the reaction vessel. After a reaction time of 120 min at 210° C., the reactor was cooled immediately to room temperature by submerging it in water.

The contents of the reactor were vacuum filtered and the solids washed with 300 mL of boiling water to remove any unreacted scavenger as well as byproducts from the pretreatment. The volume and pH of the filtrate were recorded and the pretreated biomass was stored in an airtight bag at 8° C. for further use and analysis.

The content of glucan, mannan, acid-soluble and acid-insoluble lignin in the pretreated biomass as well as sugar concentrations in the autohydrolysis liquor were determined according to NREL standard procedures (Sluiter & Hames et al., 2006; Sluiter et al., 2008). However, owing to the small amount of biomass used in the pretreatment, the procedures were downscaled by a factor of 56. All analyses were done in triplicate.

Enzymatic hydrolysis was carried out according to a NREL standard procedure (Selig, Weiss et al., 2008). Deviating from this procedure, the sodium citrate buffer was added as to obtain a pH of 5.0 and a sodium azide concentration of 0.005 mol/L after sample preparation. 230 μL of Accelerase 1500 enzyme complex, with an activity of 26 FPU/mL were added to each vial. This corresponds to an enzyme dosing of 60 FPU/g cellulose. The enzymatic hydrolysis of the samples was carried out continuously for 120 hours in an INFORS HT Minitron incubator at 50° C. and a shaking speed of 210 min$^{-1}$. The concentration of sugars in the supernatant was determined with HPLC.

III. Effect of Autohydrolysis Additives

In the following, the present invention will be explained with the help of representative experiments. In particular, the effectiveness of the described carbocation scavengers in autohydrolysis for improving the digestibility of the resulting cellulose is demonstrated. Compared to a state of the art autohydrolysis treatment, the digestibility of the cellulose can be improved. The yields of the enzymatic hydrolysis for each compound are benchmarked against such a control sample (no scavenger) where a yield of 64.8% was obtained.

It is important to recall that the concentration of all tested scavengers was equivalent, in molar terms, to 4% w/w 2-naphthol (0.2054 mol scavenger/mol lignin C9 unit). The yield obtained with this concentration of 2-naphthol, which is an already known effective scavenger, is shown for comparison, too. The newly described scavengers have a different mode of action and can be more effective than 2-naphtol.

The pH of the filtrates recovered from the treatments with the different additives showed very similar pH (3.02-3.15), indicating that there were no differences in the autohydrolysis environment for the generation of carbocations.

Figure 7:
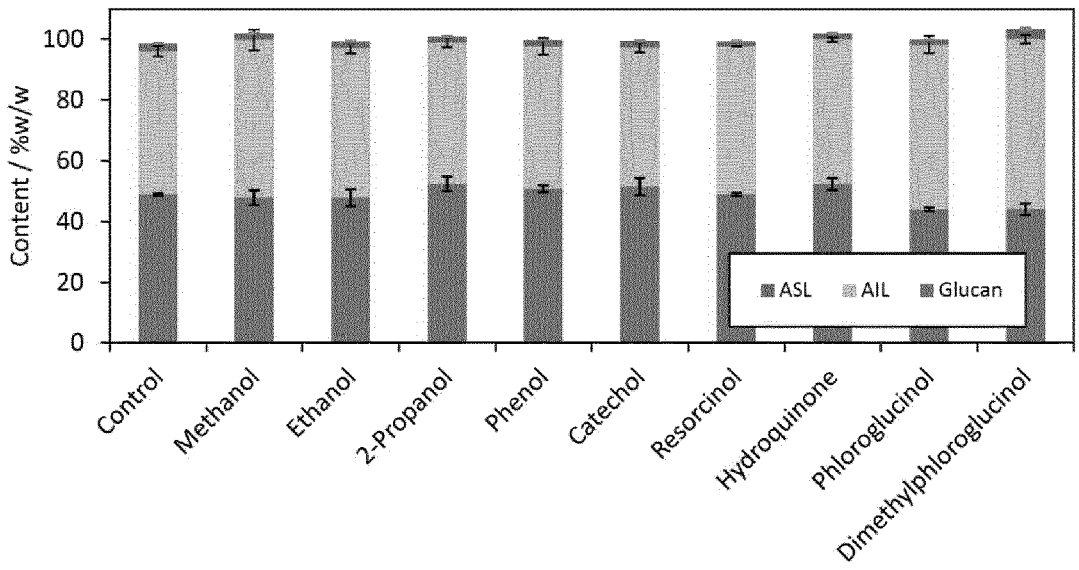
FIG. 7 a first diagram showing the scavenging effect of different tested compounds by means of the wood composition after hydrolytic treatment.

The composition of the various samples after autohydrolysis with the different additives is shown in FIG. 7. It can be observed that hemicellulose was removed completely, which is typical for an autohydrolysis treatment. Samples showed similar contents of cellulose and lignins except for biomass pretreated with phloroglucinol and dimethylphloroglucinol, which showed a noticeably higher content of acid insoluble lignin (AIL) than the others. This is due to the incorporation of these very reactive additives into the lignin structure.

Figure 8:
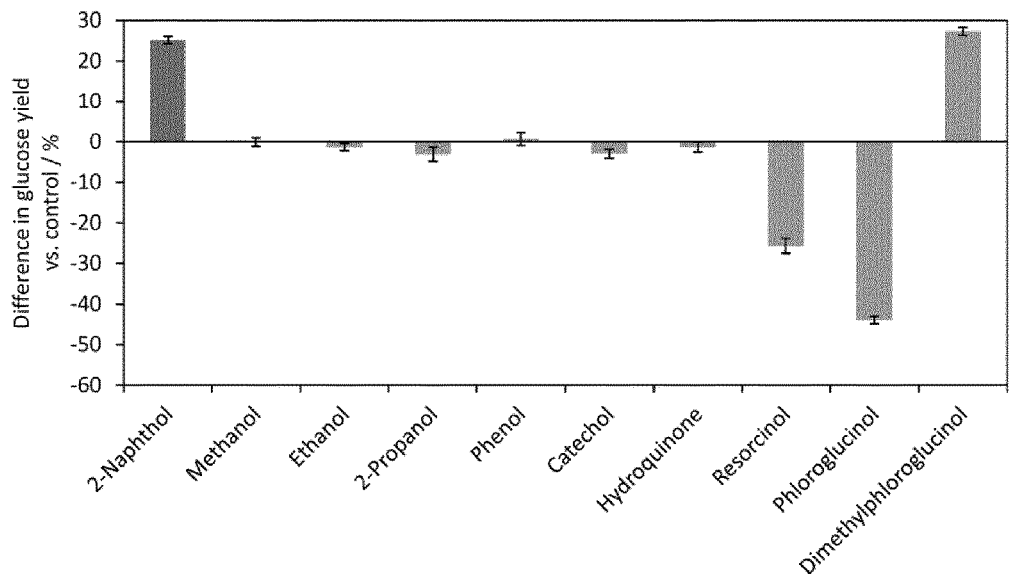
FIG. 8 a second diagram showing the scavenging effect of different tested compounds by means of glucose yield after hydrolytic treatment.

The glucose yields obtained in the enzymatic hydrolysis after 120 hours are shown in FIG. 8. It can be observed that aliphatic alcohols did not have an effect on the glucose yield of the enzymatic hydrolysis. The likely explanation for this is that they are simply too weakly nucleophilic and thus unable to avoid repolymerization reactions (i.e. the carbocations were mostly attacked by other lignin structures and not by the alcohol). The conclusion from these results is that alcohol scavengers have to be activated more towards electrophilic substitution to have an effect, aliphatic alcohols are not reactive enough.

One option therefore is to make use of aromatic groups, since an aromatic ring with its high electron density can enhance the affinity to the positively charged carbocations. The results with aromatic alcohols show interesting relationships between the structure of the molecules and their reactivity. Phenol shows no effect, probably also because it is not reactive enough and cannot prevent lignin repolymerization to a large enough extent. This is interesting with regard to the fact, that in an autohydrolysis-delignification process phenol did indeed have a significant positive effect on lignin extraction (Lora & Wayman, 1980). This also demonstrates the fundamental difference in the working principle of an extraction process to the biochemical degradation process presented in this document.

Figure 9:
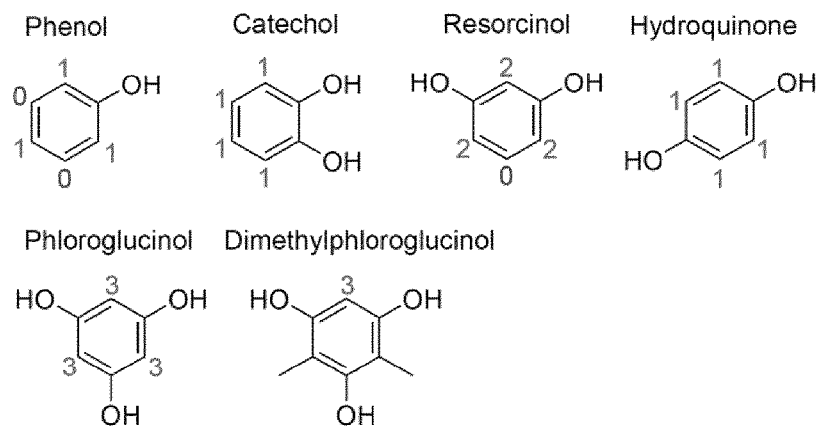
FIG. 9 structures of different compounds tested for their scavenging activity and their respective activation positions.

The addition of another OH group to the phenol molecule would be expected to increase the overall reactivity of the molecule, but not all positions are equally reactive because the hydroxyl groups direct substitutions towards ortho and para positions relative to them. This is shown in FIG. 9. It is likely that only the free positions of resorcinol, which receive the positive mesomeric effect from both OH groups and not just from one (as in catechol and hydroquinone), are reactive enough to compete with lignin structures in attacking the formed carbocations. This explains why practically no effect was observed from phenol, catechol and hydroquinone.

However, because resorcinol has three reactive positions, it can undergo several substitutions and promotes the crossing of lignin molecules. This results in more condensed lignin structures and explains the significant worsening of the yield during the enzymatic hydrolysis. This explanation is further supported by results obtained with phloroglucinol, which showed an even larger decrease in the yield of the hydrolysis than resorcinol. Phloroglucinol has a similar structure to resorcinol (OH groups in meta position to each other) but its three free positions are even more reactive as they are activated by three OH groups. This results in more crossing reactions and in even more condensed structures, explaining the dramatic worsening of the glucose yield in the enzymatic hydrolysis.

In summary, it is necessary that the added substances be highly nucleophilic in order to be able to participate in reactions with carbocations formed in the lignin structure. Aliphatic alcohols and monocyclic aromatic alcohols with ring positions that are activated just by a single OH group (e.g. phenol, catechol) are not reactive enough. Aromatic alcohols with ring positions activated by two or more OH groups (e.g. resorcinol, phloroglucinol) do indeed react but act as crossing agents, worsening the glucose yield of the enzymatic hydrolysis.

In this line of thought, a resorcinol- or phloroglucinol-derived molecule with just a single reactive site should prove as a very effective scavenger. When methylating two of the three free ring positions in phloroglucinol, dimethylphloroglucinol is obtained which has just a single ring position available for the reaction with the lignin carbocation. Indeed, dimethylphloroglucinol proved as a very effective additive. The cellulose conversion was increased to 92.1%, meaning dimethylphloroglucinol is even a more effective additive than the known scavenger 2-naphtol (compare FIG. 8). No compound has been known so far which can suppress lignin condensation in autohydrolysis as effective or even more than 2-naphtol.

This new class of scavengers is based on the activation of an aromatic ring position by several (at least two) OH groups and the simultaneous sterical blocking/deactivation of excessive reactive sites. In distinction to this class of scavengers, 2-naphtol is composed of two aromatic rings and just one OH group. I particular, its scavenging effect is based on the preservation/loss of aromaticity of its aromatic ring system.

Figure 10:
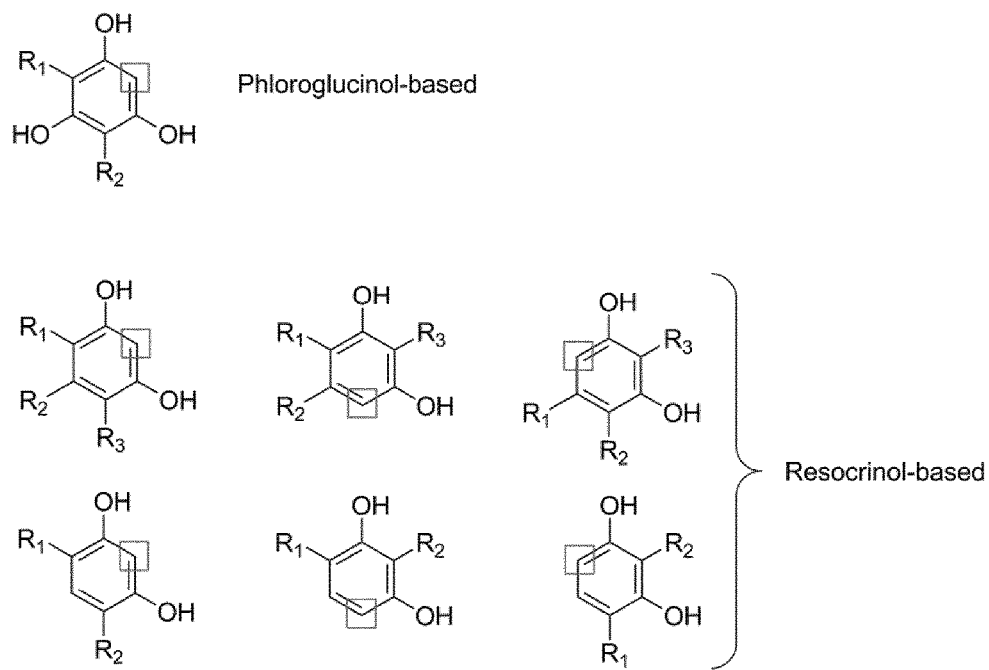
FIG. 10 structures of further scavenging compounds according to the invention.

This new class of scavengers offers possible alternatives to 2-naphthol, which are molecules based on resorcinol or phloroglucinol with occupying/blocking excessive reactive sites by covalent bonds (see FIG. 10).

IV. References

1997. IUPAC. Compendium of Chemical Terminology. 2nd ed. in: *IUPAC. Compendium of Chemical Terminology*, (Eds.) A. D. McNaught, A. Wilkinson, Blackwell Scientific Publications. Oxford Alvira, P., Tomás-Pejó, E., Ballesteros, M., Negro, M. J. 2010. Pretreatment technologies for an efficient bioethanol production process based on enzymatic hydrolysis: A review. *Bioresource Technology*, 101(13), 4851-4861.

Berlin, A., Balakshin, M., Gilkes, N., Kadla, J., Maximenko, V., Kubo, S., Saddler, J. 2006. Inhibition of cellulase, xylanase and β-glucosidase activities by softwood lignin preparations. *Journal of Biotechnology*, 125(2), 198-209.

Dorrestijn, E., Laarhoven, L. J. J., Arends, I. W. C. E., Mulder, P. 2000. The occurrence and reactivity of phenoxyl linkages in lignin and low rank coal. *Journal of Analytical and Applied Pyrolysis*, 54(1-2), 153-192.

Esteghlalian Ali, R., Srivastava, V., Gilkes, N., Gregg David, J., Saddler John, N. 2000. An Overview of Factors Influencing the Enzymatic Hydrolysis of Lignocellulosic Feedstocks. in: *Glycosyl Hydrolases for Biomass Conversion*, Vol. 769, American Chemical Society, pp. 100-111.

Knut, L., Rolf, L. 1972. Acid degradation of lignin. Part VII. The cleavage of ether bonds. *Acat Chem. Scand.*, 24(10), 2005-2023.

Li, J., Gellerstedt, G. 2008. Improved lignin properties and reactivity by modifications in the autohydrolysis process of aspen wood. *Industrial Crops and Products*, 27(2), 175-181.

Li, J., Henriksson, G., Gellerstedt, G. 2007. Lignin depolymerization/repolymerization and its critical role for delignification of aspen wood by steam explosion. *Bioresource Technology*, 98(16), 3061-3068.

Li, X., Ximenes, E., Kim, Y., Slininger, M., Meilan, R., Ladisch, M., Chapple, C. 2010. Lignin monomer composition affects *Arabidopsis* cell-wall degradability after liquid hot water pretreatment. *Biotechnology for Biofuels*, 3, 1-7.

Lora, J. H., Wayman, M. 1980. Simulated autohydrolysis of aspen milled wood lignin in the presence of aromatic additives. Changes in molecular weight distribution. *Journal of Applied Polymer Science*, 25(4), 589-596.

Mosier, N., Wyman, C., Dale, B., Elander, R., Lee, Y. Y., Holtzapple, M., Ladisch, M. 2005. Features of promising technologies for pretreatment of lignocellulosic biomass. *Bioresource Technology*, 96(6), 673-686.

Palonen, H., Tjerneld, F., Zacchi, G., Tenkanen, M. 2004. Adsorption of *Trichoderma reesei CBH I and EG II* and their catalytic domains on steam pretreated softwood and isolated lignin. *Journal of Biotechnology*, 107(1), 65-72.

Pan, X., Xie, D., Gilkes, N., Gregg, D., Saddler, J. 2005. Strategies to enhance the enzymatic hydrolysis of pretreated softwood with high residual lignin content. *Applied Biochemistry and Biotechnology*, 124(1), 1069-1079.

Radt, F. 1950. in: *Elsevier Encyclopedia of Organic Compounds*, (Ed.) F. Radt, Vol. Series III Volume 12B, Elsevier. New York.

Sarkanen, K. V., Ludwig, C. H. 1971. *Lignins: occurrence, formation, structure and reactions/edited by K. V. Sarkanen [and] C. H. Ludwig*. Wiley-Interscience, New York.

Satoshi, K., Richard, G., John, K. 2005. Lignin-Based Polymer Blends and Biocomposite Materials. in: *Natural Fibers, Biopolymers, and Biocomposites*, CRC Press.

Selig, M., Weiss, N., Ji, Y. 2008. Enzymatic saccharification of lignocellulosic biomass—Laboratory analytical procedure (LAP), NREL/TP-510-42629. National Renewable Energy Laboratory.

Sluiter, A., Hames, B., Ruiz, R., Scarlata, C., Sluiter, J., Templeton, D. 2006. Determination of sugars, byproducts, and degradation products in liquid fraction process samples, NREL/TP-510-42623. National Renewable Energy Laboratory.

Sluiter, A., Hames, B., Ruiz, R., Scarlata, C., Sluiter, J., Templeton, D., Crocker, D. 2008. Determination of structural carbohydrates and lignin in biomass, NREL/TP-510-42618. National Renewable Energy Laboratory.

Sluiter, A., Ruiz, R., Scarlata, C., Sluiter, J., Templeton, D. 2005. Determination of extractives in biomass, NREL/TP-510-42619. National Renewable Energy Laboratory.

Studer, M., DeMartini, J., Davis, M., Sykes, R., Davison, B., Keller, M., Tuskan, G., Wyman, C. 2011. Lignin content in natural Populus variants affects sugar release. *Proc Nat Acad Sci USA*, 108, 6300-6305.

Studer, M. H., Pielhop, T., Rudolf von Rohr, P. 2013. Use of carbonium ion scavengers in the treatment of lignocellulosic biomass, (Ed.) E. Zurich, Vol. WO/2013/068092, Pielhop, Thomas. Switzerland.

Voitl, T., Nagel, M. V., Rudolf von Rohr, P. 2009. Analysis of products from the oxidation of technical lignins by oxygen and H3PMo12O40 in water and aqueous methanol by size-exclusion chromatography. *Holzforschung*, 64(1), 13-19.

Wade, L. G. 2006. *Organic Chemistry*, 6th ed. Prentice Hall.

Wayman, M., Lora, J. H. 1978. Aspen autohydrolysis—The effects of 2-naphtol and other aromatic compounds. *Tappi*, 61(6), 55-57.

The invention claimed is:

1. A process for the production of a cellulosic feedstock by hydrolytic treatment of lignocellulosic biomass wherein at least one compound is added to the lignocellulosic biomass during at least one of before, during or after the aqueous treatment autohydrolysis of the lignocellulosic biomass, wherein the compound is selected from at least one compound of

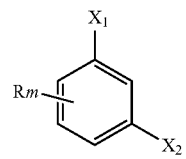

the general formula (II)

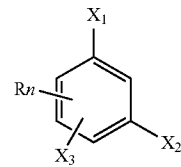

wherein
$X_1$, $X_2$, $X_3$=OH,
R=unsubstituted or substituted alkyl substituent(s) or unsubstituted or substituted alkenyl substituent(s), and
n=2.

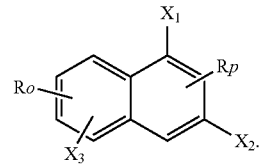

2. The process according to claim 1, wherein the aqueous treatment of the lignocellulosic biomass is a liquid hot water treatment or an aqueous steam treatment.

3. The process according to claim 1, wherein lignocellulosic biomass consists of lignocellulosic material containing fermentable carbohydrate.

4. The process according to claim 1, wherein the aqueous treatment autohydrolysis of the lignocellulosic biomass is carried out under inert gas, oxygen containing, ozone containing or hydrogen containing atmosphere.

5. The process according to claim 1, wherein the aqueous treatment autohydrolysis of the lignocellulosic biomass is carried out in a temperature range from 100 to 260° C., and at a pressure within the range from 0 to 500 bar.

6. The process according to claim 1, wherein the pH during the aqueous treatment of the lignocellulosic biomass is adjusted by the addition of at least one acid.

7. The process according to claim 1, wherein the pH during the aqueous treatment of the lignocellulosic biomass is adjusted by the addition of at least one base.

8. The process according to claim 1, wherein the water to dry biomass ratio is in the range between 1:5 and 100:1.

9. The process according to claim 1, wherein the at least one compound used as scavenger is added an amount between 0.01 to 20% w/w based on dry biomass loading.

10. The process according to claim 1, wherein any unreacted scavenger compound is recovered after autohydrolysis treatment and recycled to the autohydrolysis treatment stage.

11. The process according to claim 1, wherein the reacted scavenger compound is recovered after autohydrolysis with a laccase treatment and recycled to the autohydrolysis treatment stage.

12. The process according to claim 1, wherein the hydrolytically treated lignocellulosic biomass is washed before entering the enzymatic hydrolysis stage.

13. The process according to claim 1, wherein the lignocellulosic biomass comprises lignocellulosic material containing fermentable carbohydrate comprising at least one of softwood spruce, hardwood beech, herbs or agricultural residues.

14. The process according to claim 1, wherein the aqueous treatment autohydrolysis of the lignocellulosic biomass is carried out under inert gas or air.

15. The process according to claim 1, wherein the aqueous treatment autohydrolysis of the lignocellulosic biomass is carried out in a temperature range from 190 to 240° C.

16. The process according to claim 1, herein the aqueous treatment autohydrolysis of the lignocellulosic biomass is carried out at a pressure within the range from 1 to 40 bar.

17. The process according to claim 1, wherein the pH during the aqueous treatment of the lignocellulosic biomass is adjusted by the addition of at least one inorganic acid which comprises nitric acid, hydrochloric acid, phosphoric acid or mixtures thereof.

18. The process according to claim 1, wherein the pH during the aqueous treatment of the lignocellulosic biomass is adjusted by the addition of at least one organic acid which comprises acetic acid, formic acid or mixtures thereof.

19. The process according to claim 1, wherein the pH during the aqueous treatment of the lignocellulosic biomass is adjusted by the addition of at least one inorganic base which comprises at least one alkali salt.

20. The process according to claim 19, wherein the alkali salt comprises sodium hydroxide.

21. The process according to claim 1, wherein the pH during the aqueous treatment of the lignocellulosic biomass is adjusted by the addition of at least one organic base which comprises pyridine.

22. The process according to claim 1, wherein the water to dry biomass ratio is in the range between 1:1 and 5:1.

23. The process according to claim 1, wherein the compound is:

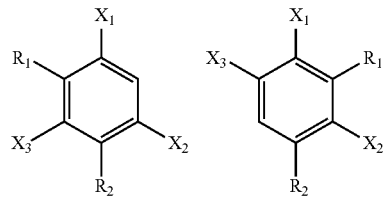

wherein $R_1$ and $R_2$ have the meaning of R and are the same or different.

24. The process according to claim 1, wherein each R is independently selected from a $C_1$-$C_{10}$ alkyl substituent or a $C_1$-$C_{10}$ alkenyl substituent.

25. The process according to claim 1, wherein each R is independently selected from a $C_1$-$C_5$ alkyl substituent or a $C_1$-$C_5$ alkenyl substituent.

26. The process according to claim 1, wherein each R is independently selected from a methyl, ethyl, n-propyl, i-propyl, n-butyl, i-butyl, t-butyl, propenyl, butenyl or pentenyl substituent.

27. The process according to claim 1, wherein the compound comprises dimethylphloroglucinol.

28. The process according to claim 1, wherein the compound is dimethylphloroglucinol.

29. A cellulosic feedstock or lignin fraction obtainable by a process according to claim 1.

* * * * *

UNITED STATES PATENT AND TRADEMARK OFFICE
CERTIFICATE OF CORRECTION

PATENT NO. : 10,370,501 B2  Page 1 of 1
APPLICATION NO. : 15/317293
DATED : August 6, 2019
INVENTOR(S) : Philipp Rudolf von Rohr et al.

It is certified that error appears in the above-identified patent and that said Letters Patent is hereby corrected as shown below:

In the Claims

Column 16, Lines 51-59, Claim 1, after n=2. delete " 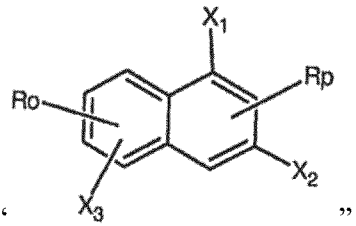 "

Signed and Sealed this
Third Day of March, 2020

Andrei Iancu
*Director of the United States Patent and Trademark Office*